United States Patent
Reicher

(10) Patent No.: US 10,579,234 B2
(45) Date of Patent: Mar. 3, 2020

(54) SYSTEMS AND USER INTERFACES FOR OPPORTUNISTIC PRESENTATION OF FUNCTIONALITY FOR INCREASING EFFICIENCIES OF MEDICAL IMAGE REVIEW

(71) Applicant: MERGE HEALTHCARE SOLUTIONS INC., Hartland, WI (US)

(72) Inventor: Murray A. Reicher, Rancho Santa Fe, CA (US)

(73) Assignee: MERGE HEALTHCARE SOLUTIONS INC., Hartland, WI (US)

(*) Notice: Subject to any disclaimer, the term of this patent is extended or adjusted under 35 U.S.C. 154(b) by 248 days.

(21) Appl. No.: 15/261,719

(22) Filed: Sep. 9, 2016

(65) Prior Publication Data

US 2018/0075188 A1 Mar. 15, 2018

(51) Int. Cl.
| | |
|---|---|
| *G06F 3/01* | (2006.01) |
| *G06F 3/0481* | (2013.01) |
| *G06F 3/0484* | (2013.01) |
| *G06F 19/00* | (2018.01) |
| *G16H 30/40* | (2018.01) |
| *G16H 40/60* | (2018.01) |
| *G16H 10/60* | (2018.01) |
| *G16H 50/70* | (2018.01) |
| *G16H 50/20* | (2018.01) |

(52) U.S. Cl.
CPC ........ *G06F 3/04842* (2013.01); *G06F 3/0481* (2013.01); *G06F 3/04845* (2013.01); *G16H 10/60* (2018.01); *G16H 30/40* (2018.01); *G16H 40/60* (2018.01); *G16H 50/20* (2018.01); *G16H 50/70* (2018.01); *G06F 3/013* (2013.01)

(58) Field of Classification Search
CPC .... G06F 19/321; G06F 3/013; G06F 3/04842; G06F 3/0481
See application file for complete search history.

(56) References Cited

U.S. PATENT DOCUMENTS

| | | | |
|---|---|---|---|
| 9,113,781 B2 | 8/2015 | Wels et al. | |
| 9,818,231 B2 | 11/2017 | Coffey et al. | |
| 2005/0289472 A1* | 12/2005 | Morita | G06F 3/011 715/757 |
| 2007/0226211 A1* | 9/2007 | Heinze | G06F 17/30011 |

(Continued)

OTHER PUBLICATIONS

Shawn N. Murphy et al., "High Throughput Tools to Access Images from Clinical Archives for Research", Journal of Digital Imaging, vol. 28(2), pp. 194-204, 2015, PMC.

*Primary Examiner* — Shourjo Dasgupta
(74) *Attorney, Agent, or Firm* — Michael Best & Friedrich LLP

(57) ABSTRACT

Systems and techniques are disclosed for opportunistic presentation of functionality for increasing efficiencies of medical image review, such as based on deep learning algorithms applied to medical data. One of the methods includes a user interface that displays, in a first portion of the user interface, one or more medical images associated with a patient. Widgets selected from a multitude of widgets are displayed in a second portion of the user interface, with the selection being based on a context associated with the user interface. User input associated with each interaction with the displayed widgets are responded to, and the first portion or second portion are updated in response to the received user input.

17 Claims, 9 Drawing Sheets

(56) References Cited

U.S. PATENT DOCUMENTS

| | | | |
|---|---|---|---|
| 2009/0274384 A1* | 11/2009 | Jakobovits | G06F 19/321 382/254 |
| 2010/0131482 A1 | 5/2010 | Linthicum et al. | |
| 2010/0305965 A1* | 12/2010 | Benjamin | G06Q 50/22 705/2 |
| 2011/0201900 A1* | 8/2011 | Zhang | G16H 15/00 600/300 |
| 2011/0214055 A1* | 9/2011 | Georgiev | G06F 19/00 715/702 |
| 2012/0191793 A1 | 7/2012 | Jakobovits | |
| 2012/0278105 A1 | 11/2012 | Luszcz et al. | |
| 2013/0006650 A1* | 1/2013 | Bocirnea | G06Q 10/10 705/2 |
| 2013/0249702 A1* | 9/2013 | Terai | A61B 5/743 340/691.6 |
| 2014/0005550 A1* | 1/2014 | Lu | G16H 40/63 600/459 |
| 2015/0049081 A1 | 2/2015 | Coffey et al. | |
| 2015/0324087 A1* | 11/2015 | Gregory | G06F 3/0488 345/174 |
| 2015/0347682 A1* | 12/2015 | Chen | G16H 50/30 705/2 |
| 2016/0147946 A1* | 5/2016 | Von Reden | G16H 10/60 705/3 |
| 2016/0310099 A1* | 10/2016 | Hamano | A61B 6/4233 |
| 2017/0032092 A1* | 2/2017 | Mink | G06F 19/3418 |

* cited by examiner

| IBM Watson 500 | Q Filter by Clinical Concern 522 | ✉ Contact Patient | 📋 To Do List |
|---|---|---|---|
| Possible Diagnosis 502 | Problem List 508    6 | Medications 514    7 | Recommended Actions 516   3 |
| COPD 504<br>Very Likely | Shortness of Breath | Lisinopril PO<br>40 mg: Once per day | Colonoscopy |
| Asthma<br>Questionable | Wheezing | Tiotropium<br>2.5 mg: Once per day | Chest X-Ray in 3 months |
| Bronchitis<br>Questionable | Fever | Carvedilol<br>25 mg: Twice per day | Echocardiogram in 6 months |
| Lung Cancer<br>Unlikely | Chest Cancer | Atorvastatin PO<br>20 mg: Once per day | Social History 518    5 |
| Tuberculosis<br>Unlikely | Abnormal Liver Function | Fluticasone/Salmetrol<br>250 mcg/50 mcg: Once per day | Retired from Work |
| Pneumonia<br>Unlikely | Procedures 510    1 | Albuterol<br>90 mcg: 2 puffs every 6 hours P... | Former Smoker |
| Common Cold<br>Unlikely | Spirometry<br>27 Jul 2015:    4 abnormal | Furosemide PO<br>90 mcg: 2 puffs every 6 hours P... | Being Sedentary |
| Sarcoidosis<br>Unlikely | Labs 512    1 | | Using Marijuana |
| Cystic Fibrosis<br>Unlikely | 12 Apr 2015:    High 225 pg/ml | | Martial History - Divorced |
| Q Other Diagnosis 506 | | | Family History 520   6 |
| | | | Asthma |

FIG. 5A

| IBM Watson 500 | 🔍 Filter by Clinical Concern | ✉ Contact Patient 📋 To Do List 524 |
|---|---|---|
| Possible Diagnosis | Problem List 6 | Recommended Actions 3 |
| COPD 45 in 100  526 | Shortness of Breath | Colonoscopy |
| Asthma 12 in 100 | Wheezing | Chest X-Ray in 3 months |
| Bronchitis 8 in 100 | Fever | Echocardiogram in 6 months |
| Lung Cancer 1 in 1000 | Chest Cancer | Social History 5 |
| Tuberculosis 1 in 13,400 | Abnormal Liver Function | Retired from Work |
| | Procedures 1 | Former Smoker |
| | Spirometry 27 Jul 2015: 4 abnormal | Being Sedentary |
| | Labs 1 | Using Marijuana |
| | 12 Apr 2015: High 225 pg/ml | Marital History - Divorced |
| | Medications 7 | Family History 6 |
| | Lisinopril PO 40 mg: Once per day | Asthma |
| | Tiotropium 2.5 mg: Once per day | |
| | Carvedilol 25 mg: Twice per day | |
| | Atorvastatin PO 20 mg: Once per day | |
| | Fluticasone/Salmetrol 250 mcg/50 mcg: Once per day | |
| | Albuterol 90 mcg: 2 puffs every 6 hours P... | |
| | Furosemide PO 90 mcg: 2 puffs every 6 hours P... | |
| 🔍 Other Diagnosis | | |

FIG. 5B

IBM Watson 500

| Possible Diagnosis | Q COPD | | |
|---|---|---|---|
| COPD<br>Very Likely | Supporting Evidence 530 | Contradictory Evidence 532 | Watson Asks 534 |
| Asthma<br>Questionable | Shortness of Breath | Family History | White Blood Cell Count? |
| Bronchitis<br>Questionable | Wheezing | Diabetes | Enter Here    Watson Finds ▼ |
| Lung Cancer<br>Unlikey | Social History | | Known Metastases? |
| Tuberculosis<br>Unlikey | Former Smoker | | Yes   No    Watson Finds ▼ |
| Pneumonia<br>Unlikey | Medications | | |
| Common Cold<br>Unlikey | Albuterol<br>90 mcg: 2 puffs every 6 hours P... | | Watson Recommends 536 |
| Sarcoidosis<br>Unlikey | Labs | | Screening Lung Cancer CT |
| Cystic Fibrosis<br>Unlikey | AAT<br>12 Apr 2015:    High 225 pg/ml | | 30 pack year smoker \| age: 55 - 70 |
| Q Other Diagnosis | | | Order    Add to Report |

FIG. 5C

IBM Watson 500

| Possible Diagnosis | Q COPD | | |
|---|---|---|---|
| COPD Very Likely | Supporting Evidence 530 | Contradictory Evidence | Watson Asks |
| Asthma Questionable | Shortness of Breath | Family History | White Blood Cell Count? 538 |
| Bronchitis Questionable | Wheezing | Diabetes | Watson Finds ▾ |
| Lung Cancer Unlikely | Social History | | Enter Here · From Referring Physician |
| Tuberculosis Unlikely | Former Smoker | | · From Epic EMR |
| Pneumonia Unlikely | Medications | | Known Me Watson Finds ▾ |
| Common Cold Unlikely | Albuterol 90 mcg: 2 puffs every 6 hours P... | | Yes │ No |
| Sarcoidosis Unlikely | Labs | | Watson Recommends 536 |
| Cystic Fibrosis Unlikely | AAT 12 Apr 2015: High 225 pg/ml | | Screening Lung Cancer CT |
| Q Other Diagnosis | | | 30 pack year smoker │ age: 55 - 70 |
| | | | Order │ Add to Report |

FIG. 5D

▼ Current Exam
+ Procedures
+ Notes
- Text ⎯⎯600⎯⎯

| Report | DOCS | FORMS | SRS | DST | CCO |

[Contains] [Past Prior Findings] [Add To] [Print/FAX] [Macros]

M≡RGE

Online Images and Results at merge.com

Patient Name:    Franco Sinatra
MRI:    Age    Sex    Date    Time
97661    74    M    6/12/2014    11:25 AM
At the Request of:
CHASEN SANBORNE PROCEDURE:    MRI OF THE BRAIN WITH & WITHOUT INTRAVENOUS GADOLINUM
COMPARISON:    HEAD MRI WITH INTRAVENOUS CONTRAST, 2/11/2015 12:15 PM
INDICATIONS:    Headache
TECHNIQUE:    CT images were created without the administration of contrast material

CONTRAST:    MULTIHANCE CC
TYPEDOSE:

TECHNICAL:    EXCELLENT
QUALITY:

FINDINGS:
CEREBRUM:    No edema, hemohage, mass, acute infraction, or inappropriate atrophy
CEREBELLUM:    No edema, hemohage, mass, acute infraction, or inappropriate atrophy
BRAINSTEM:    Large right cerebellopontine angle mass
CSF SPACES:    Ventricals, cisterns and suto are appropriate for age
SKULL:    No mass or other significant lesion
SINUSES:    Limited views demostrate no significant mucostal thickening or fluid
ORBITS:    Limited views are unmarkable
OTHER:    No abnormal meningeal or parmchymal enhancement CONCLUSION:    Right meningoma vs. acoutic neuroma Page 1 of 20

FIG. 6

SYSTEMS AND USER INTERFACES FOR OPPORTUNISTIC PRESENTATION OF FUNCTIONALITY FOR INCREASING EFFICIENCIES OF MEDICAL IMAGE REVIEW

TECHNICAL FIELD

Embodiments of the present disclosure relate to systems and techniques for accessing one or more databases and providing user interfaces for dynamic interactions with medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Medical images are typically viewed by medical professionals, such as physicians, nurses, and so on, to determine proper diagnoses of patients. In general, the medical professionals can access medical images via physical copies of the medical images, or via a display configured to present digital medical images. While reviewing medical images of a patient, a medical professional can obtain some or all of the clinical history of the patient, or any other information relevant to determining a diagnosis, and determine likely diagnoses based on the entirety of the information.

SUMMARY

The systems, methods, and devices described herein each have several aspects, no single one of which is solely responsible for its desirable attributes. Without limiting the scope of this disclosure, several non-limiting features will now be described briefly.

Particular embodiments of the subject matter described in this specification can be implemented so as to realize one or more of the following advantages. A system can present a user interface that includes both (1) medical images of a patient and (2) widgets that provide information and/or functionality relevant to a determination of a proper diagnosis of the patient. For instance, a widget can present a clinical history of the patient in the same user interface (e.g., a particular portion of the user interface) as the medical images, allowing a reviewing user (e.g., a medical professional) to maintain focus on the user interface. Additionally, the system can select widgets to present in the user interface that are predicted to be helpful to the medical professional, and can be presented to the medical professional at a time predicted to enable the best diagnosis. For instance, the system can present (e.g., automatically present) the clinical history of the patient after the medical professional has reviewed the medical images for a threshold period of time, thus ensuring that the medical professional's opinion is not unduly swayed by the clinical history (e.g., reducing anchoring bias and thus improving a likelihood of a proper diagnosis). Certain elements of a clinical history may be displayed in a certain order, based on rules set by the reading physician or organization, sometimes acting in combination with an automated computer system that assesses factors such as the indications for an examination, the patient history, and the type of examination in order to present information in an advantageous manner. For example, for a particular class of reader, when the indication is trauma, the system may first present the details of the trauma, history of other known or suspected injuries, and specific area of symptoms, whereas if the exam was performed to assess a possible abscess, the system might first present the patients vital signs, including temperature, as well as laboratory exams relevant to the diagnosis of infection.

Furthermore, the subject matter described in this specification solves problems arising out of use of technology. For instance, through combining useful widgets and medical images on a same user interface, medical professionals are able to maintain focus on useful information in contrast to accessing electronic files to search for information. Additionally, notifications can be triggered (e.g., automatically by the system, or in response to actions of the medical professionals) and timely presented to (1) patients, (2) other medical professionals, and so on, such that vital information can be smoothly gathered and presented in the user interface described above. Additionally, this automatic presentation of widgets based on the user actions in reviewing the medical images (and/or related patient information) addresses the problem of the viewer potentially overlooking certain aspects of the medical exam, such as those that might be indicated after applying certain functionality of a particular widget, because the user doesn't appreciate that a particular functionality would be useful, the particular functionality is too difficult for the user to execute or not optimally executed, the user has limited time to review the medical exam, and/or other related limitations in current medical imaging software. For example, when a reading physician reports certain finding relative to a medical imaging exam, a widget might update the most likely diagnosis, or present additional diagnoses that frequently co-exist with the more likely diagnoses.

Embodiments of the present disclosure relate to systems and techniques for accessing data stores of medical images and displaying the medical images to efficiently provide information in an interactive user interface. Previous systems for display of, and interaction with, image data were typically inefficient at presenting medical information. Disclosed herein are systems that, according to various embodiments, advantageously provide highly efficient, intuitive, and rapid dynamic interaction with medical images (including two-dimensional images and images rendered from three-dimensional image data). The systems may include interactive user interfaces that are dynamically updated to provide rapid comparison of images and functionality offered by widgets.

Design of computer user interfaces "that are useable and easily learned by humans is a non-trivial problem for software developers." (Dillon, A. (2003) User Interface Design, MacMillan Encyclopedia of Cognitive Science, Vol. 4, London: MacMillan, 453-458.) The present disclosure describes various embodiments of interactive and dynamic user interfaces that are the result of significant development, including related development of deep-learning and artificial intelligence techniques for review of medical images. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including medical images) and may enable a user to more quickly and accurately access, navigate, assess, and digest the image data than previous systems.

Further, the interactive and dynamic user interfaces described herein are enabled by innovations in efficient interactions between the user interfaces and underlying systems and components. For example, disclosed herein are improved methods of receiving user inputs (including methods of interacting with, and selecting, images), translation and delivery of those inputs to various system components, automatic and dynamic execution of complex processes in response to the input delivery, automatic interaction among various components and processes of the system, and automatic and dynamic updating of the user interfaces (to, for example, display the relevant medical images). The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing medical image interaction technology (including, e.g., Picture Archiving and Communication Systems, Electronic Medical Record Systems, and/or the like) is limited in various ways (e.g., image review is slow and cumbersome, comparison of images is inefficient, etc.), and various embodiments of the disclosure provide significant improvements over such technology. Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic medical images, and presentation of the updates to displayed medical images via interactive graphical user interfaces. Such features are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic image data.

Additional embodiments of the disclosure are described below in reference to the appended claims, which may serve as an additional summary of the disclosure.

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, non-transitory computer-readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

Further, as described herein, various embodiments of the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 5A illustrates a user interface of an example widget that presents one or more possible diagnoses FIG. 5B illustrates the example widget with a probability associated with a likelihood of each diagnosis being accurate FIG. 5C illustrates the example widget upon selection of a diagnosis FIG. 5D illustrates the example widget for requesting information related to the patient FIG. 6 illustrates an example widget associated with a clinical history of a patient.

Figure 1:
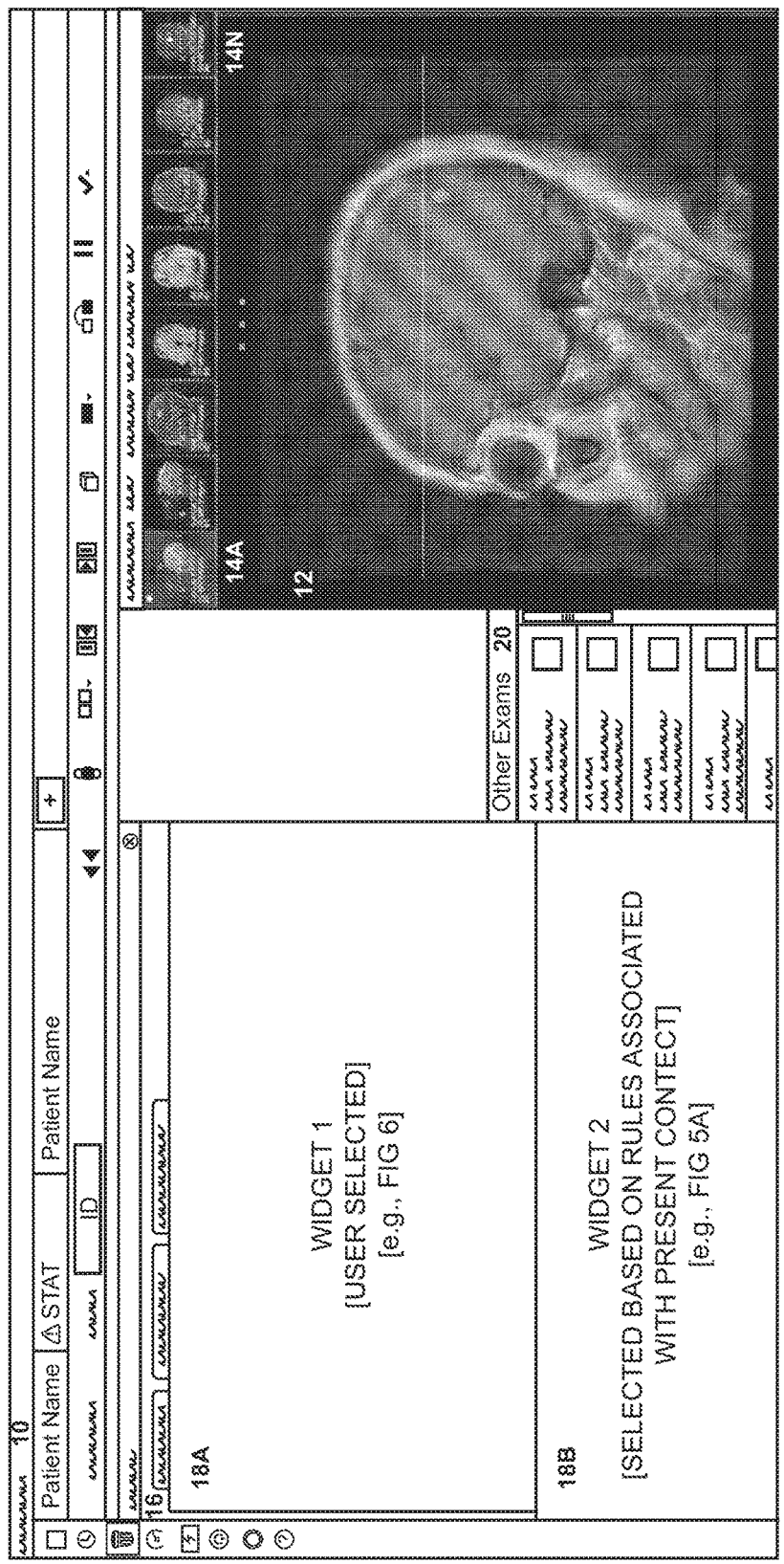
FIG. 1 illustrates an example user interface including presented widgets and medical images.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

DETAILED DESCRIPTION

This specification describes systems and user interfaces for efficient presentation of (1) medical images of patients and (2) widgets that are associated with functionality useful for determining diagnoses of the patients. In this specification, medical images include any type of image of an organism (e.g., a human patient), and may include, but are not limited to, a radiograph (e.g., an x-ray image), computed tomography (CT), magnetic resonance imaging (MRI), Ultrasound (US), mammogram, positron emission tomography scan (PET), nuclear scan (NM), pathology, endoscopy, ophthalmology, and so on.

A widget includes any user interface element that provides functionality, and can include a user interface element that displays information (e.g., causes access of one or more databases, and determination or identification of particular information), interacts with a reviewing user (e.g., receives user interactions and presents information based on the received user interactions), triggers information being provided to outside systems, user devices, or people (e.g., requests information maintained or stored by an outside system, requests that an outside system analyze information, trigger a notification to be presented on a user device of a person, and so on). A non-exhaustive list of examples of widgets can include a widget associated with presenting a clinical history of a patient, a widget associated with a 'to-do' list, a widget associated with searching for and selecting a diagnosis, a widget associated with presenting supporting and/or contradictory evidence related to a selected diagnosis based on medical records associated with a patient, a widget for searching or filtering information included in medical records, widgets associated with presenting recommendations of information to request, or test for, that can be relevant to determining accurate diagnoses, and so on. Examples of widgets are further described below, and illustrated in FIGS. 5A-6.

As will be described, a system (e.g., the medical analysis system 100 described below) can select widgets to be presented to a reviewing user in a user interface based on a context associated with the user interface, such that the selected widgets are determined (e.g., predicted) to be useful to the reviewing user while determining an accurate diagnosis. In this specification, a "context" can include any information that informs whether rules associated with presenting widgets are satisfied, and can include information associated with use of the user interface (e.g., user actions, information associated with presented medical images) and/or information associated with a user of the user interface. For instance, context can include any information describing use (e.g., by the reviewing user) of the user interface, such as a time at which the reviewing user requested medical images (e.g., particular medical images, such as a particular modality, medical images associated with a particular view, such as a craniocaudal view, and so on), actions that the user has taken with respect to the user interface (e.g., an order of the actions, identifications of the actions), attributes of the medical exam or presented medical images (e.g., DICOM data or computer aided diagnostic information), clinical history of the patient, user or system preferences, information associated with a user of the user interface (e.g., an employee role, seniority of the user) or an entity at which the user works, and so on as will be further described below.

For instance, a widget associated with presenting a clinical history of a patient can be selected by the system after a threshold amount of time of one or more medical images being presented to a reviewing user, and/or a threshold number of medical images being presented to the reviewing user. In this way, the reviewing user can consider the medical images for a period of time prior to the clinical history automatically being presented. Additionally, a widget associated with presenting particular types of information (e.g., information extracted from medical reports prepared by medical professionals, systems, or from patients) can be selected upon presentation of particular types of medical images or medical images from particular types of exams. For example, when reviewing medical images associated with a mammogram, a widget can present particular types of information to a reviewing user that are relevant to reviewing mammogram medical images. As another example, when viewing a mammogram, a widget might appear after a specified time or a specified action, such as completion of the description of the imaging findings, which may prompt the user to provide a final assessment and recommendation. The prompt may include the assessment category that is predicted by the description of the findings in combination with other factors determined by the system using artificial intelligence/machine learning, or might include recommendations also based on the combination of automated image analytics, the reported findings, the clinical history, laboratory findings, or other analyzed factors, and may also be influenced by rules set per reader, organization, exam type, or patient type. Thus, in this example, the widget presentation method may help prevent the user from prematurely arriving at an unlikely assessment or suboptimal recommendation, while also helping the user remain focused on the images until the most advantageous time.

An algorithm used by the system in automatically selecting widgets for display to the user can further depend on a particular reviewing user (e.g., the reviewing user can specify which widgets he/she is interested in viewing), a role associated with the reviewing user, an organization associated with the reviewing user, and so on. For instance, the system can present a clinical history of a patient to a senior medical professional reviewing medical images in a shorter period of time than to a junior medical professional (e.g., the junior medical professional may be more likely to base his/her opinion on the clinical history, and thus may require more time to review the medical images).

As will be described, the system can maintain rules associated with presenting widgets, which can be defined or specified by reviewing users, organizations, and so on, or can be automatically learned (e.g., by the system, or an outside system) based upon user behavior. For example, a particular medical professional may prefer that upon reviewing medical images associated with a mammogram or breast MRI, if a threshold amount of medical images are abnormal (e.g., as indicated by the medical professional, or as automatically determined by the system or an outside system), then an amount of time to present a clinical history can be increased from a baseline. In another example, the system can monitor user behavior and determine that after reviewing users perform particular actions, a threshold number of reviewing users request particular types of information, or request particular widgets be presented. The system can then store information associated with a rule describing the user behavior.

FIG. 1 illustrates an example user interface 10 including presented widgets and medical images. The user interface 10 is an example of an interactive user interface that can be generated for presentation on a user device of a reviewing user (e.g., a laptop, a tablet, a computer, a wearable device, and so on), or can be generated by a system (e.g., the medical analysis system 100 described below) and presented on a display or user device (e.g., the system can generate a document, such as a web page, for presentation on the user device). As will be described, optionally a user device can be in communication with the system, and can generate user interface 10 (e.g., the user device can execute an application, or render information) and can receive information from the system for inclusion in the user interface 10.

The user interface 10 includes a first portion 12 that includes a medical image, which can be selected from a multitude of medical images 14A-14N related to a particular patient. As illustrated in the example of FIG. 1, the reviewing user has selected a medical image associated with 'MR Brain w/Contrast'. Optionally, the first portion 12 can include multiple medical images, and the reviewing user select from the multitude of medical images 14A-14N. Similarly, multiple medical images can be presented in the first portion 12 upon selection of a particular medical image. That is, the multiple medical images may be related to the selected medical image, and the system can present them for reviewing by the reviewing user. For example, the multiple images may have been obtained during a same exam of the patient as the selected medical image, the multiple images may have been captured at a same time, or within a threshold amount of time, as the selected medical image (e.g., imaging equipment may have captured the multiple images at the same time, with each image being from a different 'slice' or view), and so on. The medical images 14A-14N available for selection can be modified according to examinations that they are associated with, and the reviewing user can select a different examination 20 such that medical images from the different examination can be accessed (e.g., in one or more databases) and representations of the medical images included in the user interface 10 for selection.

The user interface 10 further includes a second portion 16, adjacent to the first portion 162 (e.g., as illustrated, the second portion 16 can be positioned to the left of the first portion 16) that presents widgets 18A-18B to the reviewing user. Optionally, the second portion 16, or any widget included in the second portion 16, can be movable by the reviewing user to be located at a different position within the user interface 10. For instance, the reviewing user can interact with a display (e.g., via a mouse or keyboard), or touch screen display presenting the user interface 10, and can drag (e.g., after a long-press, or with greater than a threshold force or pressure on the touch screen) the second portion 16 or widget to a new position.

As illustrated, the second portion 16 includes a first widget 18A selected by the reviewing user. For example, the reviewing user can utilize the user interface 10 to specify a particular widget from a multitude of widgets that is to be included in the second portion 16. For instance, the reviewing user can interact with the user interface 10 to cause presentation, on the user interface 10, of a list of widgets available to presented. Similarly, the list of widgets can include widgets that are predicted to be useful to the reviewing user, and the reviewing user can select a widget for inclusion in the second portion 16. Optionally, the reviewing user can access search functionality included in the user interface 10, and describe a particular widget to be included.

Similarly, the second portion 16 includes a second widget 18B selected by the system according to algorithms (e.g., deep learning, artificial intelligence, etc.) or rules indicating widgets predicted to be useful based on a context associated with the user interface 10. In some embodiments, widgets may be selected for display based on the same or similar Computer Aided Processing ("CAP") as are discussed in U.S. application Ser. No. 14/139,068, filed Dec. 23, 2013, and titled "INTELLIGENT MANAGEMENT OF COMPUTERIZED ADVANCED PROCESSING," which is hereby incorporated by reference in its entirety for all purposes. For example, a significant finding of a CAP may trigger the system discussed herein to automatically display a corresponding widget and/or automatically execute functionality associated with the widget.

As described herein, the rules can be specified by each medical professional, by an organization, or learned based on monitoring user behavior of medical professionals (e.g., as will be described below). To select a second widget 18B based on the rules, the system can monitor the user interface 10, including times at which user actions are performed, times at which medical images are initially presented or cycled through to other medical images, and so on, and select a widget for inclusion in the user interface 10. Optionally, particular rules can be based on information associated with the medical professional using the user interface 10, such as a role of the medical professional, a seniority of the medical professional, preferences of the medical professional, and so on. As an example, the system can determine that a widget presenting a clinical history of the patient is to be selected after a threshold amount of time (e.g., 15 seconds, 20 seconds, a user selectable amount of time) subsequent to the medical images 12 being presented. As another example, the system can determine that particular information about the patient is to be included in the second portion 16 upon the medical professional describing his/her findings. For instance, the system can present demographic information after the medical professional describes his/her findings, so that the demographic information doesn't influence the description (e.g., but can influence an ultimate diagnosis).

Examples of widgets are described above, and are described below with respect to FIGS. 5A-6. As an example of a widget (e.g., a widget illustrated in FIG. 5A), multiple potential diagnoses can be presented to the reviewing user along with information indicating a likelihood of each diagnosis being true (e.g., a numerical likelihood, or descriptive text indicating a likelihood such as very likely, unlikely, and so on). The widget can be presented in the second portion 16 after the reviewing user reviews the medical images for a threshold period of time, and optionally after one or more of the reviewing user reviewing a medical history of the patient, a clinical history of the patient, and so on. The widget can include a summary of information related to the patient, such as a list of problems being experienced by the patient, lab work associated with the patient, and so on. Additionally, the widget can include recommendations to the medical professional regarding additional questions to ask the patient, additional lab work to have performed, and any other information determined to be relevant in properly diagnosing the patient. As will be described, an outside system (e.g., a system, such as WATSON, associated with machine learning) can analyze information associated with the patient, and determine the recommendations (e.g., based on medical literature, journals, monitored medical professional behavior, and so on).

While the example user interface 10 includes two widgets 18A-18B, any number of widgets can be presented to the reviewing user, and optionally the presented widgets can be removed and new widgets included based on rules indicating widgets predicted to be useful. Optionally, the system can determine (e.g., based on the rules) that a particular widget is to be included in the second portion 16, and can initially prompt the user to confirm that the particular widget be displayed. In this way, the reviewing user can ensure that widgets are presented upon his/her authorization, and can further select a widget to be removed so that the confirmed widget can be included in its place.

Figure 2:
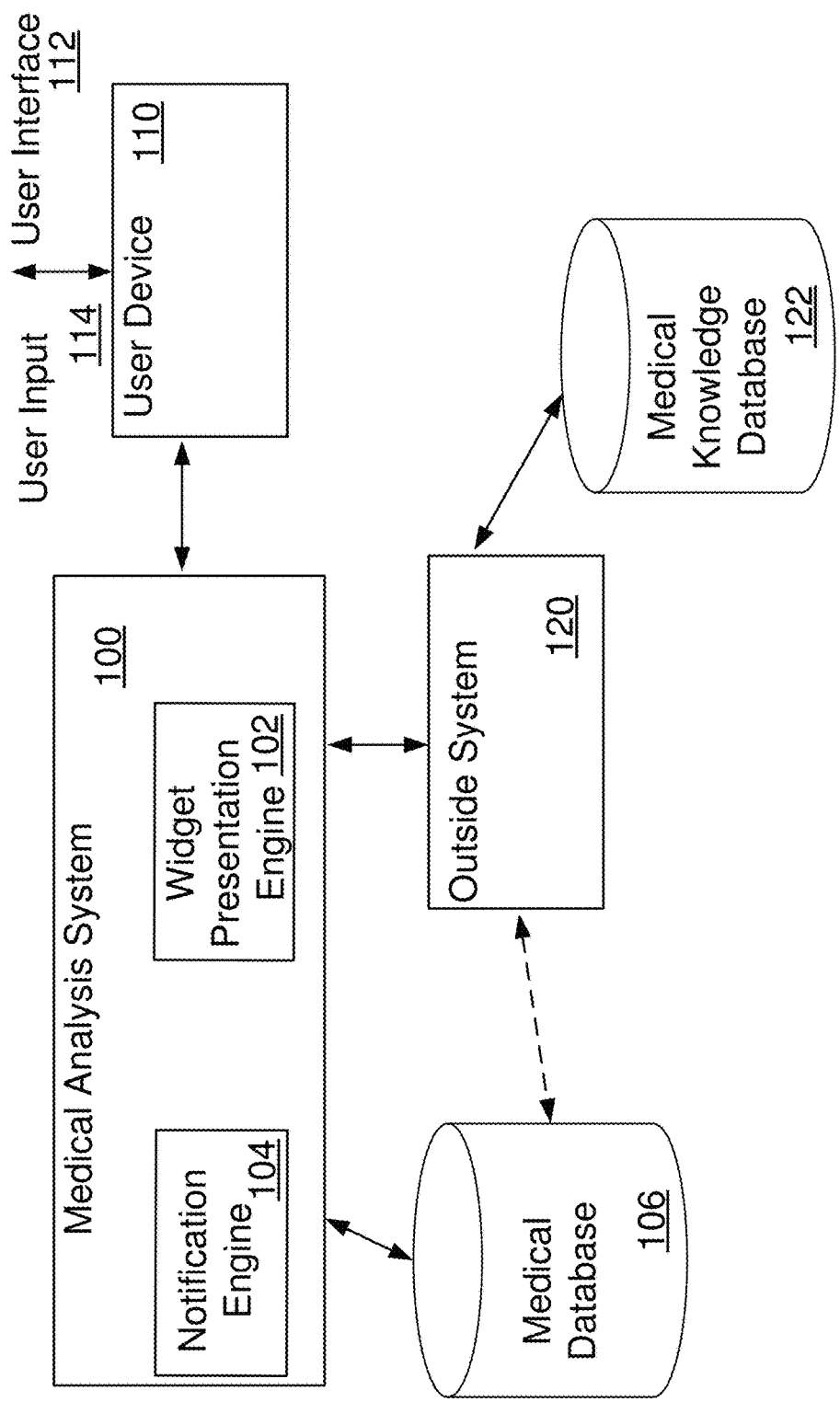
FIG. 2 illustrates an example block diagram of a medical analysis system in communication with other systems and components.

FIG. 2 illustrates an example block diagram of a medical analysis system 100 in communication with other systems and components. The medical analysis system 100 can be a system of one or more computers, or one or more virtual machines executing on a system of one or more computers, and can be in communication with a user device 110 (e.g., a user device comprising one or more hardware processors, such as a laptop, tablet, computer, or optionally a display in communication with the medical analysis system 100) and one or more databases 106 or storage subsystems (e.g., storing medical images of patients, medical histories of patients, medical reports, and so on).

As described above, the medical analysis system 100 can generate user interface information 112 for presentation on the user device 110, or optionally the user device 110 can generate user interface information 112 and receive information from the medical analysis system 100 for inclusion in the user interface 110. For instance, the user device 110 can execute an application, and present a user interface (e.g., the user interface 10 described above). The user device 110 can receive information from the medical analysis system 100 indicating particular widgets to present, and the user device 110 can access user interface data associated with the indicated widgets. Optionally, the user device 110 can perform some or all of the functionality of the medical analysis system 100 (e.g., the user device can select widgets according to rules based on use of the user interface 110, and can request that the medical analysis system 100 perform particular functionality, such as determining recommendations for information relevant to determining a diagnosis).

The medical analysis system 100 can access the databases (e.g., medical database 106) and obtain medical images for presentation on the user device 110 (e.g., selected medical images as described above with respect to FIG. 1). Similarly, the medical analysis system 100 can utilize the databases to obtain or extract information associated with a patient, such as problems or ailments indicated by the patient, medication being taken by the patient, family history of the patient, social history of the patient, and so on. The information associated with the patient can be presented in the user interface 112 or otherwise utilized by the medical analysis system 100 (e.g., according to functionality of presented widgets). Additionally, the medical analysis system 100 can update information associated with the patients, such as including diagnoses specified by a reviewing user, and so on.

The medical analysis system 100 includes a widget presentation engine 102 that can monitor use of the user interface 112 presented on the user device 110, and can determine selections of widgets predicted to be useful to a reviewing user of the user device 110 according to one or more rules. As described above, the rules can be specified by reviewing users, entities or organizations associated with reviewing users or associated with determining best practices, or the rules can be learned by the widget presentation engine 102 through monitoring of user behavior. Specifying and determining rules is described in more detail below, with respect to FIG. 3. The widget presentation engine 102 can monitor a context associated with the user interface 112, such as use of the user interface 112 by a reviewing user of the user device 110, and can determine whether one or more rules are satisfied. Optionally, each rule can include logic, such as triggers associated with actions of reviewing users (e.g., user selections of records, clinical histories, medical images, types of medical images, recordations of notes or findings, notifications being sent by reviewing users to patients or other medical professionals, and so on), which the widget presentation engine 102 can utilize to determine whether a rule is satisfied. Similarly, each rule can indicate presentation of a particular widget upon satisfaction of the rule.

The widget presentation engine 102 can cause presentation of one or more widgets in the user interface 112, and upon presentation, the reviewing user can interact with the widgets according to functionality afforded by each widget. That is, each widget can be associated with particular functionality, and the reviewing user can interact with the widget (e.g., provide user input 114 or other information, for instance medical images, audio recordings, medical analysis equipment readings such as an electrocardiogram, and so on, can be dragged onto a presented widget or a location of the other information can be indicated), and the medical analysis system 100, or optionally the user device 110, can affect the functionality associated with the widget (e.g., access one or more local databases, access one or more outside systems over a local network or the internet, perform calculations, determine recommendations, and so on).

The medical analysis system 100 further includes a notification engine 104 that can generate notifications to be provided to outside systems, user devices, and so on. For instance, a particular widget presented in the user interface 112 may include a selectable option to contact a patient or a medical professional. The notification engine 104 can access information associated with the patient (e.g., preference information), and can generate notifications to be provided as an email, a text message, described in an automated phone call, or provided as information for receipt by an application (e.g., an 'app' downloaded from an electronic application store) executing on the patient's user device (e.g., mobile phone).

Similarly, the particular widget can allow for the reviewing user to include one or more medical images or other images, audio, video, and so on, in the notifications. Optionally the notification engine 104 can request information from a medical professional, and generate notifications to be provided to an email account of the medical professional, or provided as a text message or phone call. Additionally, the notification engine 104 can provide notifications that activate on a user device (e.g., laptop, computer, mobile device) of the medical professional and can include information associated with a request for the medical professional to perform an action (e.g., perform lab work, obtain measurements, and so on). Optionally, the notifications that activate on a user device of the medical professionals can be included in a user interface (e.g., the user interface 10 as described in FIG. 1) that illustrate a same, or similar, user interface as the user interface 112 (e.g., same medical images the reviewing user was reviewing, and so on). In some embodiments, a notification sent to a user device automatically activates an application on the user device (e.g., a standalone application associated with medical image viewing or a messaging application) and displays a link from which the user can access further information regarding the notification, the medical images, the patient, etc., such as through an Internet communication with the medical analysis system 100 discussed herein.

An outside system 120 (e.g., a system of one or more computers, or optionally software executing on the medical analysis system 100, which can be in communication with an outside system over a network such as the internet) can be utilized to implement functionality afforded by one or more of the widgets (e.g., widgets described below, with respect to FIG. 5A-5D). The outside system 120 can implement deep machine learning software (e.g., neural networks), such as WATSON, and can be in communication with one or more databases or storage subsystems (e.g., the medical knowledge database 122) that stores information informing proper diagnoses of patients based on relevant factors, and any information relevant to medicine. As will be described, a widget can present likelihoods of one or more diagnoses being accurate with respect to a particular patient, which can be based on information determined by the outside system. Additionally, the widget can present information and factors in conformance with, or in opposition to, a diagnosis selected by a reviewing user (e.g., the widget can receive information determined by the outside system based on information associated with the patient, such as a medical history, clinical history, and so on). The outside system 120 can further determine recommendations of information to obtain regarding the patient (e.g., lab work such as a white blood cell count) that can better inform whether a selected diagnosis is accurate, and can present the information in a widget. The notification engine 104 can generate notifications in response to the reviewing user interacting with the widget (e.g., to request the recommended information, such as by providing the notification to a patient informing the patient to have a white blood cell count check performed).

Figure 3:
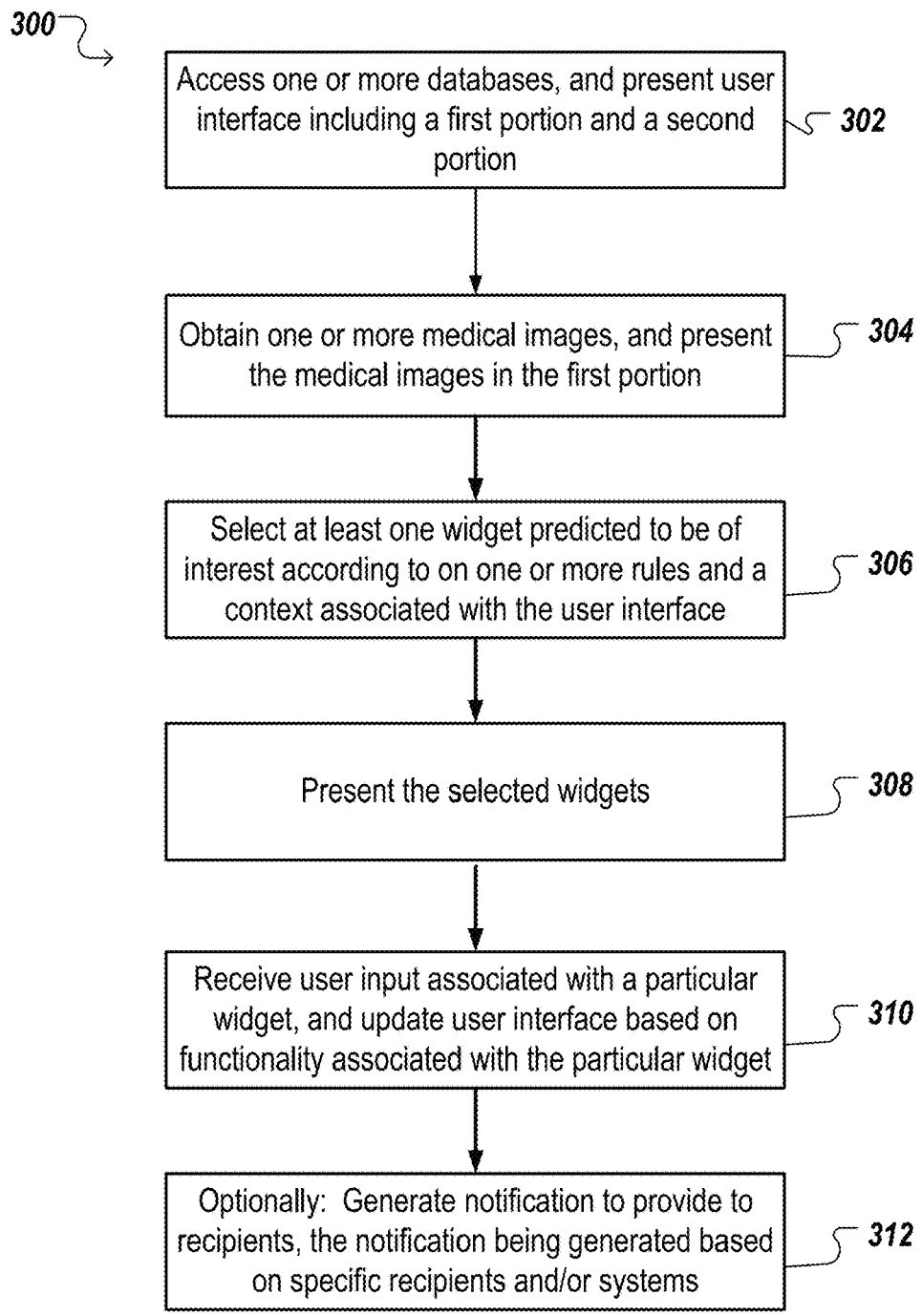
FIG. 3 is a flowchart of an example process for presenting widgets and medical images in a user interface.

FIG. 3 is a flowchart of an example process 300 for presenting widgets and medical images in a user interface. For convenience, the process 300 will be described as being performed by a system of one or more computers (e.g., the medical analysis system 100). Optionally, and as described above, one or more, or all of the, features of the process 300 can be performed by a user device in communication with the system.

The system accesses one or more databases and presents a user interface including a first portion and a second portion (block 302). As described above, and illustrated in FIG. 1, the system presents a user interface that includes (1) medical images and (2) one or more widgets that are each associated with performance of particular functionality, such as providing a medical history of a patient, providing a clinical history of a patient, extracting and presenting information from medical reports, providing a 'to-do' list in which a reviewing user (e.g., a doctor or other medical professional) can specify actions that are to be taken with respect to the patient or actions that are to be taken to determine a proper diagnosis of the patient, and so on. Optionally, a widget can analyze medical images, and present a zoomed-in portion of the medical images that illustrates potential anomalies or areas of the medical images that are to be further reviewed. Optionally, and as will be further described below with respect to FIG. 5A-5D a widget can receive information from, and provide information to (e.g., user inputted information), an outside system associated with machine learning.

The user interface is, in some implementations, advantageously separated into distinct portions, such that a reviewing user can maintain focus on medical images in a first portion, while widgets automatically present themselves in a second portion based on context. In this way, the reviewing user can interact with the widgets at opportune moments to reduce cognitive biases, including anchoring bias, satisficing bias, availability bias, framing bias, and so on. As will be described below, one or more rules can be associated with the triggering of widgets based on context of the user interface, such as use of the user interface and optionally information associated with the reviewing user. Through advantageously triggering widgets at opportune moments to reduce bias, known cognitive biases can be reduced thus providing more accurate diagnoses of patients through use of the simple technologically based user interfaces described herein. Furthermore, based on rules, the widgets may move to the image display area at opportune times so that the reviewing physician does not need to move his/her head or eyes to access the presented information or functionality. As a result, the reader may require less saccadic eye movement, thus reducing fatigue and perhaps enhancing a mental state of flow. For instance, widgets may be presented at particular locations within the user interface, such as for an example widget, at a top portion of the user interface (e.g., the portion that includes widgets) such that the reviewing user may simply move his/her gaze to the portion and view the widget, without having to look down also. Optionally, rules may indicate locations at which to place widgets and can be based on context information, such as, for example, the current location of the display at which the user is determined to be viewing (e.g., based on the last portion of the user interface interacted with by the user). For example, the system may determine that the reviewing user is interacting with a top portion of medical images, and place a widget similarly at a top portion of the user interface (e.g., in the widget portion of the user interface), near a current cursor location, last viewed image/pane, etc. Optionally, widgets may be positioned on top of, or adjacent to, medical images, which can be specified in the rules.

The system obtains medical images and presents the medical images in a first portion of the user interface (block 304). The system can receive information identifying a particular patient to be reviewed, for instance the reviewing user can enter a name associated with the patient into the user interface, and the system can access databases to obtain medical images for review. As illustrated in FIG. 1, the medical images are presented in a particular portion of the user interface (e.g., the right side of the user interface in the example of FIG. 1, however the medical images can be presented in other locations and can be user-selectable).

The system selects a widget predicted to be of interest to the reviewing user according to on one or more rules and based on a context associated with the user interface (block 306). As described above, the system presents widgets in the user interface that are predicted to be of use to the reviewing user, and that also are determined to reduce cognitive biases associated with diagnosing patients.

The system monitors the reviewing user's use of the user interface, including times at which user actions occurred (e.g., opening of medical images, selecting of particular medical images, a speed at which medical images are reviewed before subsequent medical images are requested), particular types of user actions performed (e.g., selections of medical images, requesting clinical history, and so on), and determines whether rules associated with presenting widgets are satisfied based on the monitored user actions. Optionally, the system can monitor a reviewing user's eye-gaze and determine portions of the user interface the reviewing user has reviewed (e.g., the system can determine whether the reviewing user has reviewed each medical image sufficiently prior to the reviewing user requesting a subsequent medical image, and so on).

As an example, the system can monitor a time at which the reviewing user is first presented with medical images, and after a threshold amount of time, can present a widget that presents a clinical history (e.g., clinical summary) of the patient. As described above, the threshold amount of time can be user-selectable, and can optionally be determined to represent an amount of time that optimally reduces any cognitive biases associated with reading a clinical history. For instance, the system can monitor diagnoses indicated by reviewing users, and can monitor the diagnoses over time to determine whether they change, and through correlating user actions on the user interface to whether diagnoses changed, can determine likely sources of cognitive biases that may have negatively affected the reviewing user's decisions. In this way, the system can determine that reviewing user's, in general, are to review medical images for a determined amount of time prior to clinical history being presented.

Similarly, the system can monitor the reviewing user's actions, and upon the reviewing user interacting with the user interface to request that a report (e.g., a particular medical report) be presented, the system can present the clinical history of the patient. This system can also monitor the actions of other users to determine behaviors that are associated with more efficient or accurate reading, and can then suggest to a particular reader how to modify presentations or rules in order to promote better outcomes. For example, U.S. patent application Ser. No. 15/074,268, titled "INTELLIGENT DYNAMIC PRELOADING AND PROCESSING," filed on Mar. 18, 2016, which is hereby incorporation by reference in its entirety for all purposes, describes examples of tracking user behaviors based on ordering of images and automating subsequent display of images, each of which may be used in conjunction with the various systems and methods discussed herein.

As another example, the system can analyze medical images for anomalies, and can present a widget that includes a focused in portion of a medical image with information indicating a type of anomaly detected. Since the system presenting such analyzed information to the reviewing user may be helpful, but may also persuade the reviewing user that the portion is indeed anomalous, the system may present the widget after one or more of (1) a threshold amount of time of reviewing of one or more of the medical images, clinical history, passing (2) the reviewing user first locating the anomalous area (e.g., the system may confirm his/her findings), (3) the reviewing user not locating the anomalous area, and optionally utilizing his/her gaze to determine whether the reviewing user focused on the determined anomalous area for a threshold period of time, and so on.

As described above, each rule can include arbitrary context information (e.g., user actions, and so on, as described above) and can be associated with a particular reviewing user (e.g., a rule can be specific to when the particular reviewing user is using the user interface), an organization (e.g., a rule can be associated with use of the user interface by reviewing users associated with a particular hospital or other organization), a particular role (e.g., a rule can be associated with particular types of reviewing users, such as radiologists, general practitioners, and so on), a particular type of exam that produced medical images, an experience level of the reviewing user, and so on. In this way, presentation of widgets can be fine-grained and tailored to situations and reviewing users, thus ensuring that a one-size fits all approach is avoided and reducing cognitive bias.

While the above description included examples of rules and associated widgets that are presented or triggered in response to rules being determined to be satisfied, the description is non-exhaustive and the rules can be made arbitrarily complex or to include any information that can be monitored to determine a time at which they are satisfied. For instance, a rule might indicate that upon a reviewing user viewing a medical image, indicating that the medical image is anomalous, viewing a subsequent medical image (e.g., a medical image of the anomalous portion from a different view), indicating the subsequent medical image is anomalous, and optionally selecting a diagnosis, then a widget is to be presented that describes a family history of the patient (e.g., a family history of a particular type of cancer). Similarly, the rule can be specific to a particular reviewing user, users associated with a particular employee role, users that have particular specialties, users that work for particular organizations, and so on. Rules for selection and/or presentation of widgets may be executed periodically (e.g., every x seconds), continuously (e.g., using interrupts), in response to certain triggers (e.g., movement of the mouse, placement of a notation, etc.), or at other intervals. Thus, in some embodiments widgets are selected and displayed in real-time in response to satisfaction of the conditions associated with the corresponding widget rule.

The system presents the selected widgets (block 308). As described above, upon determining that one or more widgets are to be selected, the user interface is updated with the selected widgets in a second portion of the user interface. In addition to the widgets selected above, the user can request one or more widgets be presented in the second portion (e.g., the user can select from a drop-down menu, verbally describe one or more actions they wish to perform, such as viewing a medical report, and so on). Optionally, the user interface can block one or more widgets from being presented if the reviewing user has not sufficiently reviewed the medical images (e.g., the reviewing user may request a clinical summary be presented, and the system can present information indicating that the reviewing user is to review the medical images longer).

The system receives user input associated with a particular widget and updates the user interface based on functionality associated with the particular widget (block 310). The system can receive user input, such as a touch screen interaction, a mouse click, text entered, audio of the reviewing user (e.g., speech), an image, file, or audio, being provided to the particular widget (e.g., dragged to the particular widget), and so on. The system then updates the user interface according to the functionality afforded by the particular widget. For instance, a widget associated with presenting a clinical history may be updated based on the reviewing user scrolling through the clinical history. A different widget may be associated with analyzing medical images (e.g., the widget can cause the system to utilize one or more computer vision processes, such as producing a false color version, determine outlines of anomalous objects, and so on), and the reviewing user can drag a medical image to the different widget, or utilizing a stylus, finger, mouse, select a portion of a displayed medical image and draft the portion to the different widget.

The system optionally generates notifications (block 312). As described above, with reference to FIG. 2, the system can generate notifications to be provided to particular recipients and can generate notifications based upon preferences associated with the recipients and/or based on types of information to be included in the notification. For instance, utilizing a presented widget the reviewing user can indicate that the patient is to be notified about a diagnosis selected by the reviewing user. The reviewing user can include a particular medical image, or portion of medical image, in a notification to the patient. Optionally, the notifications can include information to trigger an application executing on a user device or system of a recipient, such that the application presents the notification in a similar user interface as described above with respect to FIGS. 1 and 3, or includes a portion of the information included in the user interface (e.g., the notification can trigger the user device or system to present particular portions of medical images, clinical history, and so on).

Figure 4:
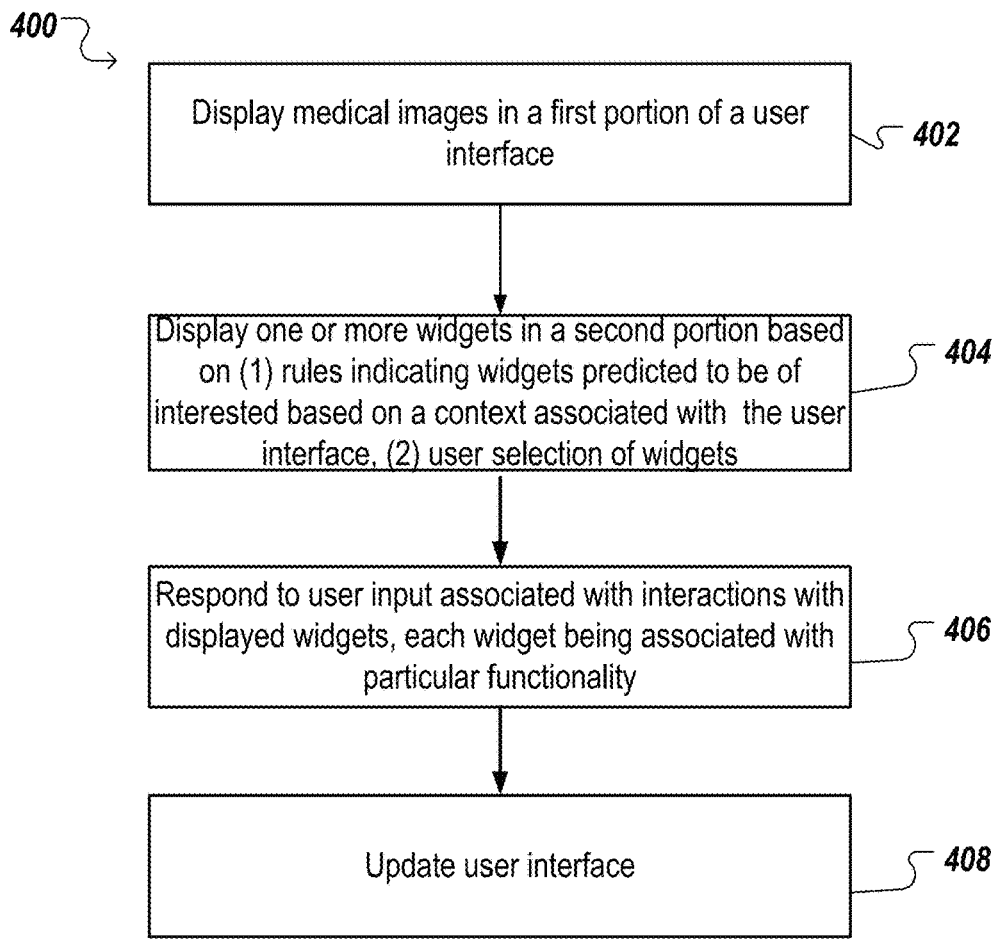
FIG. 4 is a flowchart of an example process for utilizing a user interface including medical images and widgets

FIG. 4 is a flowchart of an example process 400 for utilizing a user interface including medical images and widgets. For convenience, the process 400 will be described as being performed by a user interface being provided on a system of one or more computers (e.g., the medical analysis system 100) or a user device in communication with the system.

The user interface displays medical images in a first portion (block 402). As described above, a reviewing user (e.g., a medical professional) can request medical images associated with a patient, and the user interface can present obtained medical images in the first portion.

The user interface displays widgets in a second portion (block 404). The user interface presents widgets predicted to be useful to the reviewing user and optionally predicted to reduce cognitive biases. As described above, the widgets can include a clinical summary, a to-do list (e.g., a list associated with remaining actions to be performed), information indicating probabilities of diagnoses (e.g., described below with respect to FIG. 5A), and so on. The second portion may be advantageously separated from the first portion, such that the reviewing user may easily be able to keep his/her focus on the medical images while glancing at widgets for particular functionality.

The user interface responds to user input associated with interactions with displays widgets or medical images (block 406). As described above, with respect to FIG. 3, one or more widgets can respond to user interactions of the reviewing user, and the user interface can update in response to the user interactions. Similarly, the reviewing user can interact with displayed medical images, and the user interface can respond to the interactions, including accessing databases, networks, analyzing medical images, and so on, and updating in response.

FIG. 5A illustrates a user interface of an example widget 500 that presents one or more possible diagnoses. The widget 500 is an example of a widget that can be selected according to one or more rules (e.g., as described in FIG. 3), and can be included, for instance, in the second portion 16 of the user interface 10 illustrated in FIG. 1.

The widget 500 includes possible diagnoses 502 with an indication of a likelihood of the diagnosis being accurate given medical history, clinical history, medical images, and so on, of a patient. For instance, the diagnosis "COPD" is indicated as having a high likelihood (e.g., "Very Likely" as illustrated). An outside system, such as WATSON, can analyze information associated with the patient and determine possible diagnoses 502 with associated likelihoods. Additionally, the reviewing user can specify a particular diagnosis (e.g., through search functionality 506), and the widget 500 can update with an indication of a likelihood associated with the particular diagnosis.

The widget 500 further presents a problem list 508, indicating problems reported by the patient or determined or noticed by a medical professional. The widget 500 further presents procedures 510 that the patient has undergone along with a summary of information determined from the procedure (e.g., "4 abnormal"). Optionally, the procedures 510 can be interactive, and upon receiving user interactions (e.g., selection of "Spirometry") the widget 500 can be updated with a more detailed report from the procedure. The widget 500 further presents lab work information 512, medications the patient is on 514, social history 518 and family history 520. The reviewing user can cause a notification to be generated, for instance to the patient 522, as described above. Additionally, a to-do list 524 can be presented for the reviewing user to add any items that need to be performed.

In some embodiments, the widget 500 and/or other widgets may provide an estimated disease classification, such as progressive or stable, such as based on computer automated analysis of the medical images and/or other patient data. For example, disease classifications may be calculated as discussed in U.S. Pat. No. 9,378,331, issued on Jun. 28, 2016, and titled "Annotation and assessment of images," which is hereby incorporated by reference in its entirety for all purposes. In some embodiments, the disease state and/or other calculated attributes of a patient, such as any combination of those discussed in the above-noted patent, may be part of the widget selection algorithm or rules and, thus, used in selecting widgets for display.

The widget 500 presents recommended actions 516, which can be determined by the outside system based on the patient's medical history and best medical practices. For instance, the widget 500 can present procedures for the patient to undergo (e.g., preventative procedures), and the notifications 522 can be provided to the patient automatically, which can indicate the recommended actions 516.

FIG. 5B illustrates the example widget 500 with a probability associated with a likelihood of each diagnosis being accurate. For instance, the widget 500 presents a likelihood of "43 in 100" for "COPD", in contrast to a textual description of "Very Likely" as in FIG. 5A. Optionally, the reviewing user can toggle between the two views.

FIG. 5C illustrates the example widget 500 upon selection of a diagnosis. As illustrated above, the widget 500 can present possible diagnoses and associated likelihoods. Upon selection of a diagnosis (e.g., "COPD"), the widget 500 can present supporting 530 and contradictory 532 evidence. For instance, the outside system can review the patient's medical history, and utilizing machine learning models trained on medical knowledge, can determine aspects of the patient's medical history that support and contradict the selected diagnosis. In this way, the reviewing user can receive information supporting or denying the conclusion, and can utilize the information to further test the patient. In addition, to further ensure that the selected diagnosis is accurate, the widget can request information 534 that can be used to make a likelihood of the selected diagnosis more accurate. For instance, the widget 500 is requesting that the reviewing user obtain a white blood cell count, and based on the white blood cell count, the widget 500 can update the probabilities associated with the selected diagnosis, update the supporting 530 and contradictory 532 evidence, and so on. The widget 500 can further recommend additional procedures, lab work, and so on, that the patient should undergo. As illustrated, the widget 500 is recommending that the patient undergo a screening test for lung cancer.

FIG. 5D illustrates the example widget 500 for requesting information related to the patient. As illustrated in FIG. 5C, the widget can request information 534 to increase a likelihood of a selected diagnosis being accurate. The widget 500 can automatically (e.g., upon interaction with a user interface element 536) cause a medical history, including medical reports of the patient, to be analyzed such that the requested information can be extracted. Additionally, the widget can contact (e.g., generate notifications) to be provided to a medical professional to obtain the information.

FIG. 6 illustrates an example widget 600 associated with a clinical history of a patient. The example widget 600 is an example of a widget that can be selected based on one or more rules (e.g., as described above with respect to FIG. 3).

ADDITIONAL EMBODIMENTS

Any process descriptions, elements, or blocks in the flow diagrams described herein and/or depicted in the attached figures should be understood as potentially representing modules, segments, or portions of code which include one or more executable instructions (as described below) for implementing specific logical functions or steps in the process. Alternate implementations are included within the scope of the embodiments described herein in which elements or functions may be deleted, executed out of order from that shown or discussed, including substantially concurrently (for example, through multi-threaded processing, interrupt processing, or multiple processors or processor cores or on other parallel architectures) or in reverse order, depending on the functionality involved.

Any of the methods and processes described above may be partially or fully embodied in, and partially or fully automated via, logic instructions, software code instructions, and/or software code modules executed by one or more general purpose processors and/or application-specific processors (also referred to as "computer devices," "computing devices," "hardware computing devices," "hardware processors," and the like). For example, the methods described herein may be performed as software instructions are executed by, and/or in response to software instruction being executed by, one or more hardware processors (e.g., one or more processors of the computing system 150) and/or any other suitable computing devices. The software instructions and/or other executable code may be read from a tangible computer-readable medium. A tangible computer-readable medium is a data storage device that can store data that is readable by a computer system and/or computing devices. Examples of computer-readable mediums include read-only memory (ROM), random-access memory (RAM), other volatile or non-volatile memory devices, DVD-ROMs, CD-ROMs, magnetic tape, flash drives, and/or optical data storage devices. Accordingly, a software module may reside in RAM memory, flash memory, ROM memory, EPROM memory, EEPROM memory, registers, hard disk, solid state drive, a removable disk, a CD-ROM, a DVD-ROM, and/or any other form of a tangible computer-readable storage medium.

Additionally, any of the methods and processes described above may be partially or fully embodied in, and partially or fully automated via, electronic hardware (for example, logic circuits, hardware processors, and/or the like). For example, the various illustrative logical blocks, methods, routines, and the like described in connection with the embodiments disclosed herein may be implemented as electronic hardware, computer software, or combinations of both. To illustrate this, various illustrative components, blocks, modules, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the disclosure.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method implemented by one or more computer systems that provides an interactive user interface having functionality for viewing medical images and determining diagnoses, wherein the user interface:
   displays, in a first portion of the user interface, one or more medical images associated with a patient;
   automatically displays, in a second portion of the user interface separate from the first portion, one or more widgets selected from a plurality of widgets, the selection based on rules that specify widgets predicted to be useful for corresponding variations in context, wherein context includes one or more of: information associated with a user of the user interface, a user role of the user, an organization of the user, analytics of the user's prior actions, or analytics of other user's actions;
   responds to user input associated with interaction with the displayed widgets, wherein interactions with each widget are associated with particular functionality including (1) presentation of supporting and/or contradictory evidence related to a selected diagnosis in records associated with the patient, (2) searching for other diagnoses than the selected diagnosis, (3) searching or filtering information included in the records based on received user input, (4) causing an outside system to analyze the records and recommend additional information relevant to determining the selected diagnosis, (5) causing the outside system to determine a probability associated with the selected diagnosis based on the records; and
   updates the first portion or the second portion in response to received user input.

2. The method of claim 1, wherein the user interface updates the second portion in response to a modification of the context associated with the displayed medical images.

3. The method of claim 1, wherein the user interface receives a selection of a diagnosis related to the medical images.

4. The method of claim 1, wherein the one or more widgets are displayed at a particular location of the display determined to be nearest the user's gaze at the time of display.

5. The method of claim 1, wherein the outside system comprises one or more computer systems that are associated with machine learning based on records of a plurality of patients.

6. A method implemented by one or more computer systems, the method comprising:
   accessing one or more databases, and causing presenting user interface including a first portion and a second portion, the first portion including medical images associated with a patient obtained from the databases;
   determining one or more widgets according to rules indicating widgets predicted to be useful based on a context associated with use of the user interface, each widget being associated with particular functionality, wherein the context includes one or more of information associated with a user of the user interface, a user role of the user, an organization of the user, analytics of the user's prior actions, or analytics of other user's actions;
   causing presentation of the determined widgets in the second portion, the second portion being separate from the first portion;
   receiving user input associated with interactions with a particular widget of the determined widgets, wherein interactions with each widget are associated with particular functionality including (1) presentation of supporting and/or contradictory evidence related to a selected diagnosis in records associated with the patient, (2) searching for other diagnoses than the selected diagnosis, (3) searching or filtering information included in the records based on received user input, (4) causing an outside system to analyze the records and recommend additional information relevant to determining the selected diagnosis, (5) causing the outside system to determine a probability associated with the selected diagnosis based on the records; and
   causing updates to the user interface.

7. The method of claim 6, wherein the user interface updates the second portion in response to a modification of the context associated with the displayed medical images.

8. The method of claim 6, wherein the user interface receives a selection of a diagnosis related to the medical images.

9. The method of claim 6, wherein the method further comprises: generating a notification to be provided to a recipient, the notification being configured to activate on a user device of the recipient, and present a same user interface as the user interface.

10. The method of claim 6, wherein the context includes (1) display of a record describing a medical history of the patient, (2) a time at which the medical images are displayed, (3) selection of user interface controls associated with the selected widgets.

11. The method of claim 6, wherein the outside system comprises one or more computer systems that are associated with machine learning based on records of a plurality of patients.

12. A non-transitory computer storage medium storing instructions that when executed by a system of one or more computers, cause the one or more computers to generate a user interface having functionality for viewing medical images and determining diagnoses, wherein the user interface:
   displays, in a first portion of the user interface, one or more medical images associated with a patient;
   automatically displays, in a second portion of the user interface separate from the first portion, one or more widgets selected from a plurality of widgets, the selection being based on rules that specify widgets predicted to be useful based on a context associated with the user interface, wherein the context includes one or more of information associated with a seniority of the user;
   responds to user input associated with interaction with the displayed widgets; and
   updates the first portion or the second portion in response to received user input.

13. The computer storage medium of claim 12, wherein the user interface updates the second portion in response to a modification of the context associated with the displayed medical images.

14. The computer storage medium of claim 12, wherein the user interface receives a selection of a diagnosis related to the medical images.

15. The computer storage medium of claim 12, wherein the context includes (1) display of a record describing a medical history of the patient, (2) a time at which the medical images are displayed, (3) selection of user interface controls associated with the selected widgets.

16. The computer storage medium of claim 12, wherein interactions with each widget are associated with particular functionality including (1) presentation of supporting and/or contradictory evidence related to a selected diagnosis in records associated with the patient, (2) searching for other diagnoses than the selected diagnosis, (3) searching or filtering information included in the records based on received user input, (4) causing an outside system to analyze the records and recommend additional information relevant to determining the selected diagnosis; (5) causing the outside system to determine a probability associated with the selected diagnosis based on the records.

17. The computer storage medium of claim 16, wherein the outside system comprises one or more computer systems that are associated with machine learning based on records of a plurality of patients.

\* \* \* \* \*